United States Patent
Blacker et al.

(10) Patent No.: US 11,801,365 B2
(45) Date of Patent: *Oct. 31, 2023

(54) ROBOTIC PERCUTANEOUS DEVICE WIPER

(71) Applicant: Corindus, Inc., Waltham, MA (US)

(72) Inventors: Steven J. Blacker, Framingham, MA (US); Christopher Zirps, Sharon, MA (US); Peter Falb, Waltham, MA (US)

(73) Assignee: Corindus, Inc., Newton, MA (US)

( * ) Notice: Subject to any disclaimer, the term of this patent is extended or adjusted under 35 U.S.C. 154(b) by 476 days.

This patent is subject to a terminal disclaimer.

(21) Appl. No.: 16/847,078

(22) Filed: Apr. 13, 2020

(65) Prior Publication Data

US 2020/0297973 A1 Sep. 24, 2020

Related U.S. Application Data

(63) Continuation of application No. 15/785,366, filed on Oct. 16, 2017, now Pat. No. 10,653,863, which is a continuation-in-part of application No. 14/216,076, filed on Mar. 17, 2014, now Pat. No. 9,789,285.

(60) Provisional application No. 61/792,353, filed on Mar. 15, 2013.

(51) Int. Cl.
| | |
|---|---|
| A61M 25/01 | (2006.01) |
| A61B 34/30 | (2016.01) |
| A61B 17/00 | (2006.01) |
| A61B 34/20 | (2016.01) |
| A61M 25/00 | (2006.01) |

(52) U.S. Cl.
CPC ......... *A61M 25/0158* (2013.01); *A61B 34/30* (2016.02); *A61B 2017/003* (2013.01); *A61B 2034/2051* (2016.02); *A61M 2025/0058* (2013.01)

(58) Field of Classification Search
CPC ...... A61M 25/0158; A61M 2025/0058; A61B 34/30; A61B 2034/2051; A61B 2017/003
See application file for complete search history.

(56) References Cited

U.S. PATENT DOCUMENTS

| | | | |
|---|---|---|---|
| 3,721,252 A * | 3/1973 | Ayella | E03C 1/046 134/122 R |
| 10,046,140 B2 | 8/2018 | Kokish et al. | |
| 2002/0111585 A1 | 8/2002 | Lafontaine | |
| 2007/0260115 A1 | 11/2007 | Brock et al. | |
| 2009/0322543 A1 | 12/2009 | Crnkovich et al. | |
| 2011/0087224 A1* | 4/2011 | Cadeddu | A61B 34/73 606/49 |
| 2011/0313415 A1* | 12/2011 | Fernandez | A61M 25/0127 606/41 |
| 2012/0197200 A1* | 8/2012 | Belson | A61M 25/06 604/164.12 |
| 2014/0066899 A1 | 3/2014 | Blacker | |
| 2014/0066900 A1 | 3/2014 | Blacker | |
| 2014/0171863 A1 | 6/2014 | Blacker | |

* cited by examiner

*Primary Examiner* — Lauren P Farrar

(57) ABSTRACT

A robotic catheter system including a first drive mechanism configured to interact with an elongated medical device to cause the elongated medical device to move along its longitudinal axis. A controller provides a signal to a motor to move the first wiping surface toward the longitudinal axis when the elongated device is being withdrawn from a patient.

20 Claims, 8 Drawing Sheets

ROBOTIC PERCUTANEOUS DEVICE WIPER

CROSS-REFERENCE TO RELATED PATENT APPLICATIONS

This application is a continuation of U.S. application Ser. No. 15/785,366 entitled ROBOTIC PERCUTANEOUS DEVICE WIPER FILED Oct. 16, 2017, which is a continuation-in-part of U.S. application Ser. No. 14/216,076 entitled WIPING MECHANISM FOR A Y-CONNECTOR filed Mar. 17, 2014, now U.S. Pat. No. 9,789,285, which claims the benefit of U.S. Provisional Application No. 61/792,353 entitled WIPING MECHANISM FOR A Y-CONNECTOR filed Mar. 15, 2013 and incorporated herein by reference in its entirety.

BACKGROUND

Guide wires are used to facilitate percutaneous procedures in which the guide wire is threaded into a human patient using X-ray guidance. The guide wires are manually threaded by physician or other medical personnel but this requires that the operator be adjacent to the patient and so be in the immediate vicinity of the X-ray radiation providing the image used for guidance. Systems have been developed, such as that disclosed in U.S. Pat. No. 7,887,549 incorporated herein by reference in their entireties, which allow the guide wires to be threaded into the patient robotically and thus allow the user or operator to be remote from the patient and the X-ray radiation. When the guide wire has been threaded into a blood vessel of a human patient it may be become contaminated with blood and if it is threaded into some other type of vessel it may become contaminated with some other bodily fluid. In the course of a procedure involving a guide wire it may become useful or necessary to withdraw it through the Y-connector and/or hemostasis valve.

SUMMARY

In one embodiment a robotic catheter system includes a first drive mechanism driving a first percutaneous device along its longitudinal axis. A wiper assembly includes a first wiping engaging an outer surface of the percutaneous device along its longitudinal axis as the first percutaneous device moves relative to the wiper along its longitudinal axis. A controller provides a signal to a motor to engage the wiping surface with the outer surface of the percutaneous device while the elongated device is being withdrawn from a patient.

In one embodiment a robotic catheter system including a first drive mechanism configured to interact with an elongated medical device to cause the elongated medical device to move along its longitudinal axis. A wiper assembly includes a first wiping surface moving toward and away from the longitudinal axis. A controller provides a signal to a motor to move the first wiping surface toward the longitudinal axis when the elongated device is being withdrawn from a patient In another embodiment a wiping mechanism associated with a Y-connector and/or hemostasis valve wipes any bodily fluids which have become attached to the surface of a guide wire during its passage into a human patient as the guide wire is retracted before it enters or exits the Y-connector and/or hemostasis valve.

In a further embodiment, a method of cleaning an elongated medical device includes providing a first drive mechanism configured to interact with an elongated medical device to cause the elongated medical device to move along its longitudinal axis. A wiper assembly is provided having a first wiping surface moving toward and away from the longitudinal axis. The method further includes providing a control signal to a motor from a remote controller to move the first wiping surface toward the longitudinal axis of the elongated device when the elongated device is being withdrawn from a patient. The method also includes wiping fluid from an outer surface of the elongated medical device as the elongated medical device is begin withdrawn from the patient.

DETAILED DESCRIPTION

Figure 1:
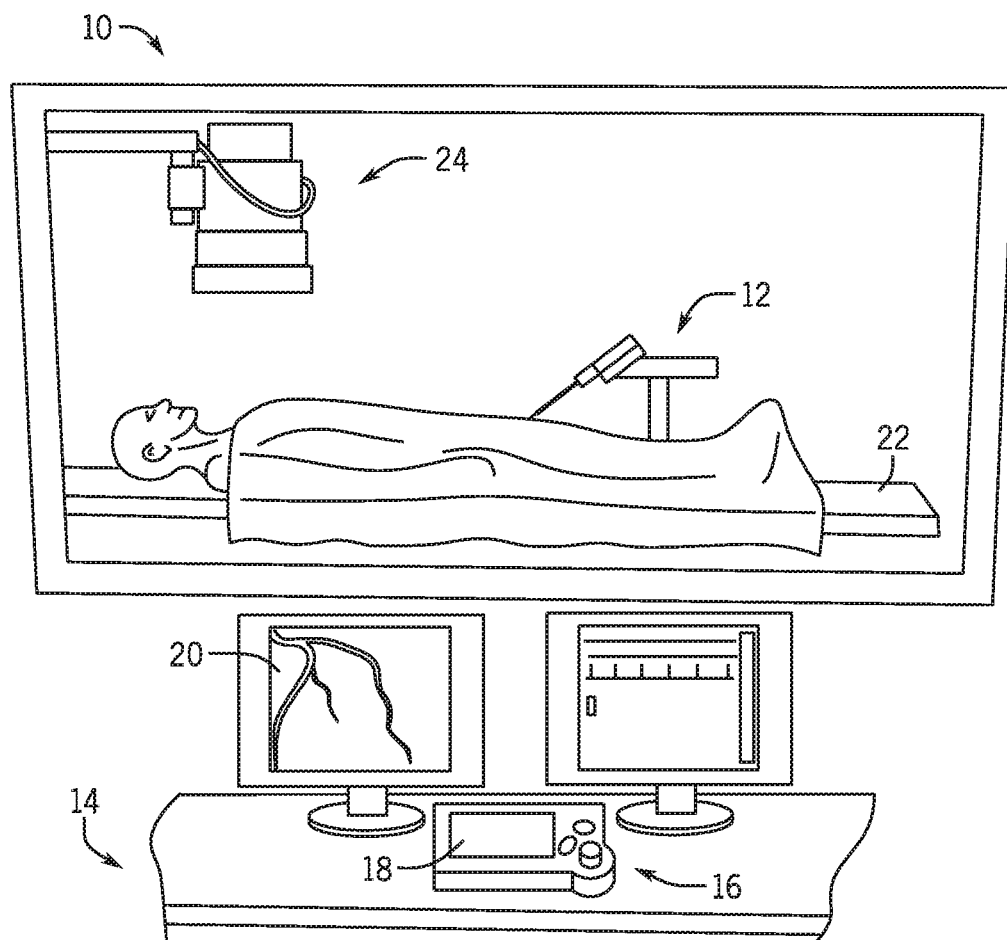
FIG. 1 is a schematic view of a wiper system proximate a hemostasis valve.

Referring to FIG. 1 a robotic system for manipulating an elongated medical device includes a bed side station 12 proximate a bed 22. A remote-control station 14 includes a controller 16 having a user input 18 to control the bed side station 12. An x-ray source 24 is used in a Fluoroscopy system to provide an image of on a display 20 in remote station 14. A robotic system such as that described in U.S. Pat. No. 7,887,549 and/or the system described in and U.S.

patent application U.S. Ser. No. 15/029,115 both of which are incorporated herein in their entireties may be used in conjunction with the wiper mechanism described herein. However, it is also contemplated that any drive system used to robotically drive a flexible percutaneous device currently known in the art or later developed may also be used in combination with the wiper systems described herein.

Figure 2:
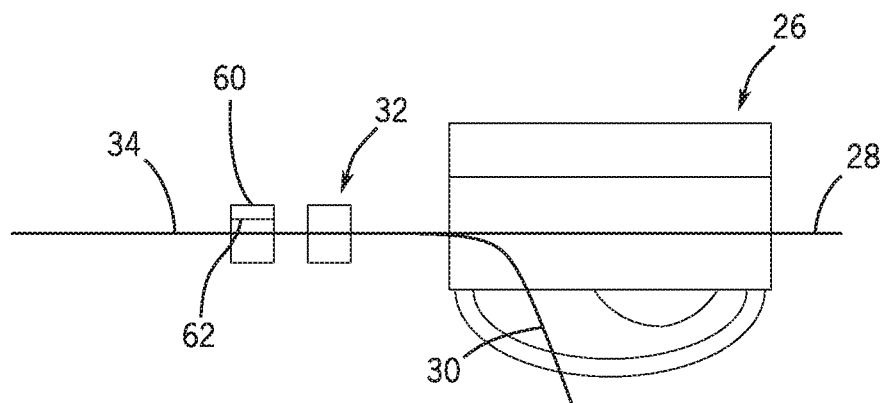
FIG. 2 to a top plan view a wiper system proximate a channel for an elongate medical device.

Referring to FIG. 2 a wiping mechanism or wiping assembly 32 may be positioned between a cassette 26 that is part of operatively connected to bed side station 12 and Y-connector and/or hemostasis valve and guide catheter. A guide wire 28 and/or working catheter 30 may be subject to wiping mechanism 32 that is deployed between the human patient and the Y-connector such that it contacts the surface of the guide wire or working catheter as it is retracted from a patient and before it interacts with the drive mechanisms of the cassette 26.

Figure 3:
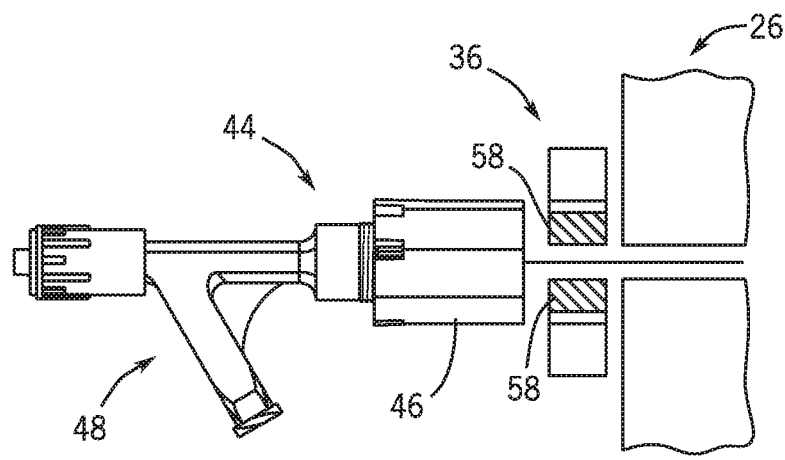
FIG. 3 is top view of a wiper mechanism at a distal portion of a cassette.

Referring to FIG. 3 a wiping mechanism assembly 36 having a wiping material 58 is positioned between the cassette 26 and the Y-connector and/or hemostasis valve assembly 44. The assembly 44 includes a Y-connector 48 having at least two legs with each having a lumen in fluid communication with one another. A hemostasis valve 46 is operatively connected to one of the legs of the Y-connector 48.

Figure 4:
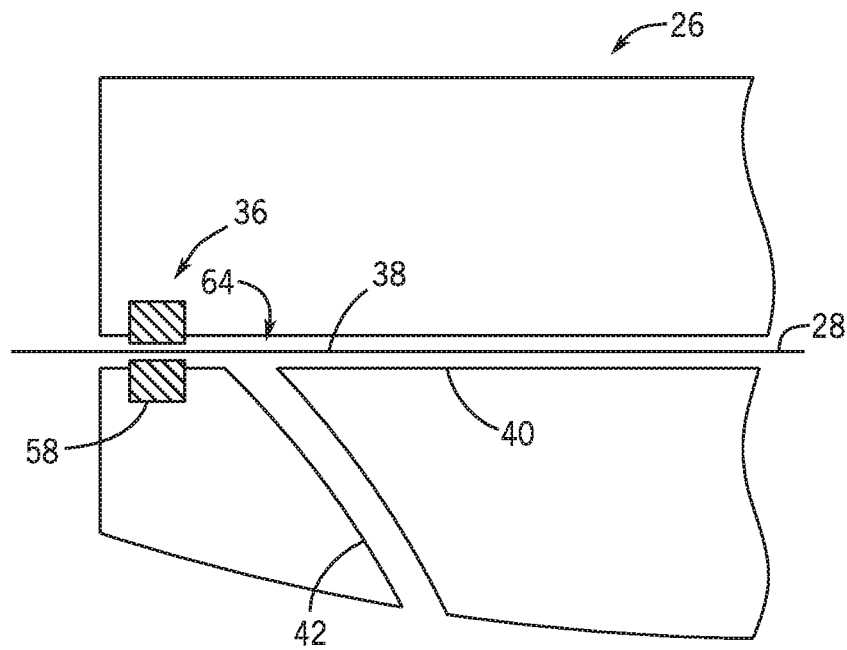
FIG. 4 is a view of the wiper mechanism intermediate a cassette and a Y-connector and hemostasis valve.

Referring to FIG. 4 in one embodiment wiping mechanism 36 is positioned within cassette 26 and intermediate a juncture 64 and the hemostasis valve assembly 44. Cassette 26 includes a first channel 40 through which guide wire 28 is operatively driven along its longitudinal axis and a second channel 42 through which a working catheter such as a balloon catheter or stent catheter is linearly driven along its longitudinal axis. Wiping mechanism 36 includes a first and second wipers 58 that move toward and away from the longitudinal axis of channel 40 to operatively engage and wipe the outer surface of guide wire 28.

Figure 5:
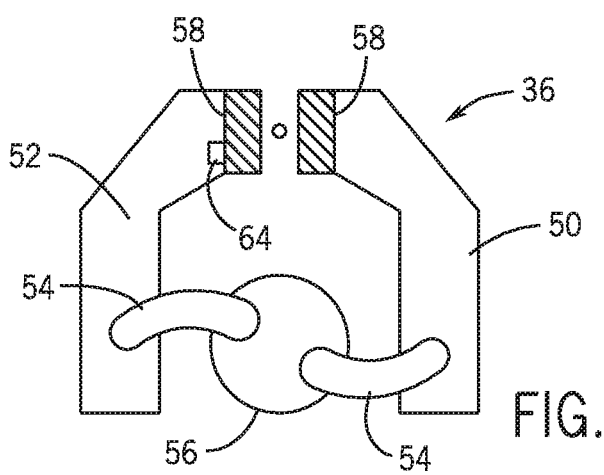
FIG. 5 is a cross sectional view of the wiper mechanism of FIG. 4.

Referring to FIG. 5 wiper assembly includes a resilient material 58 configured to wipe the outer surface of a guide wire being retracted from a patient into cassette 26 with a drive mechanism. Resilient material may be absorbent and act to wick and or wipe away fluid from the guide wire and/or working catheter as each is being withdrawn from the patient. Resilient material maybe mounted to two separate pads that are respectively attached to a first arm 50 and a second arm 52.

Arms 50 and 52 are operatively connected through linkages 54 that may be secured to a gear to drive 56. In this manner rotation of drive 56 causes the resilient opposing materials 58 to move toward and/or away from one another. The resilient pads may be robotically moved away from one another as the guide wire and/or working catheter are inserted into a patient to minimize friction to the guide wire and/or working catheter as these elongated medical devices are being inserted into a patient. The resilient pads may be robotically moved away from one another as the guide wire and/or working catheter is being withdrawn from a patient and withdrawn through the Y-connector and/or hemostasis valve.

In one embodiment the wiping mechanism involves two v-shaped members of a resilient material. In one embodiment these resilient members are connected to a mechanism which holds them out of contact with the guide wire when it is being fed forward into the human patient but which brings them into contact with the guide wire when it is being retracted into the Y-connector and/or hemostasis valve. In one embodiment these members are constructed of or carry an absorbent material such as natural or synthetic sponge such that they can absorb the bodily fluid which they wipe from the surface of the guide wire. In another embodiment an absorbent material is placed beneath or around these wiping members to absorb the bodily fluid which is wiped from the surface of the guide wire. In a further embodiment an aspiration apparatus is provided which aspirates the bodily fluid as it is wiped from the guide wire surface.

Figure 6:
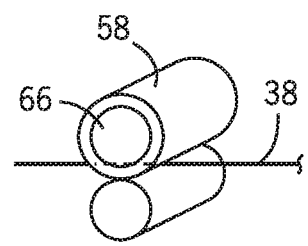
FIG. 6 is an isometric view of a roller wheel that rotates about an axis perpendicular to a longitudinal axis of an elongated medical device.

In another embodiment air may be blown over the guide wire proximate the resilient by an air curtain. In one embodiment a wiping fluid is provided by nozzles directed at the guide wire and activated when it is retracted to clean the guide wire. In this embodiment absorbent material may be provided beneath or around the guide wire to absorb the bodily fluid wiped from the guide wire by the stream of directed fluid. In another embodiment the directed fluid is air and/or a liquid and/or spray and the bodily fluid which it wipes from the guide wire is aspirated by a suction mechanism placed in the vicinity of the location on the guide wire where the air stream impinges on the wire. In one embodiment air may be directed about the percutaneous device to remove foreign particulate. In one embodiment air may be directed about the outer circumference of the precautious device to dry any liquid that was used to clean the percutaneous device as described herein. In a further embodiment, resilient material is attached to or part of roller wheels that rotates about an axis that is perpendicular to the longitudinal axis of the guide wire and/or working catheter. The rotation of the roller wheels minimizes the friction of the resilient wiping material with respect to the guide wire and/or working catheter. In one embodiment the wheel is driven by a motor when the elongated medical device is being withdrawn. In one embodiment the robotic catheter system includes a cleaner 60 depositing a fluid 62 on to the elongated medical device as the medical device is being withdrawn from the patient. In one embodiment the fluid is deposited by a remote-controlled dispenser 60 and the rate of fluid flow is determined by the controller and a function of one or more of a user input, speed in which the elongated medical device is being withdrawn. In one embodiment a sensor 64 shown in FIG. 5 is configured to sense moisture on the wiping surfaces, the sensor providing a signal to a display on a remote station to alert a user that the wiping surface is saturated. In one embodiment the controller 16 automatically provides a signal to a motor to move a wiping surface away from the elongated medical device when the drive mechanism is driving the elongated medical device into a patient. Referring to FIG. 6 a roller wheel 66 rotates about an axis perpendicular to the longitudinal axis of the elongated medical device 38.

Figure 7:
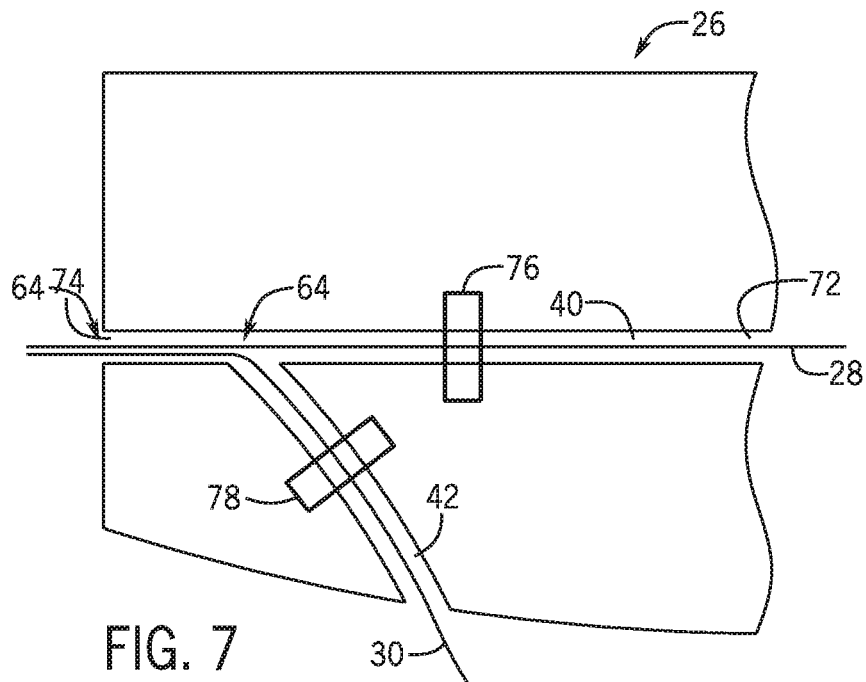
FIG. 7 is a schematic view of a robotic percutaneous system with a wiper positioned before the juncture.

Referring to FIG. 7 a cassette 26 as discussed above includes a first channel 40 through which a guide wire 28 or other flexible percutaneous device is movably driven there along from a proximal end 72 toward end and through a distal end 74 thereof. As used herein the distal end of guide wire 28 is the free end that is inserted into a vasculature. The proximal end of guide wire 28 is the free end that is outside of the patient during a procedure in the vasculature. Similarly, the distal end of the various features and mechanisms is the end that is closer to the direction that the guide wire moves toward the vasculature and the proximal end is the end or portion that is further from the vasculature.

A working catheter 30 such as a balloon catheter or stent catheter or other catheters known in the art for performing a function within a vasculature is movable driven along a second channel 42. First channel 40 and second channel 42 intersect at a juncture 64. In one embodiment first channel 40 has a longitudinal axis that is not co-linear with a longitudinal axis of channel 42. In one embodiment a first wiper assembly 76 is positioned adjacent channel 40 on the proximate side of juncture 64. Stated another way first wiper assembly 76 is positioned between juncture 64 and the proximal end 72 of cassette 26. First wiper assembly 76 operatively engages and disengages guide wire 28 as guide wire 28 is moved relative to first wiper assembly 76 along the longitudinal axis of guide wire 28. In one embodiment first wiper assembly moves a wiper element about the longitudinal axis of guide wire 28 such that it rotate about the outer surface of the guide wire. In one embodiment first wiper assembly moves both along the longitudinal axis of guide wire 28 and about the outer surface of the guide wire. In one embodiment a second wiper assembly 78 is positioned proximate channel 42 to wipe the outer surface of a working catheter 30 along the longitudinal axis of the working catheter as the working catheter is moved relative to the wiper assembly 78. As described herein below wiper assembly may move along the longitudinal axis of the working catheter or may be stationary as the working catheter 30 moves along its longitudinal axis as the working catheter 30 is moved in and/or out of the vasculature.

Figure 8:
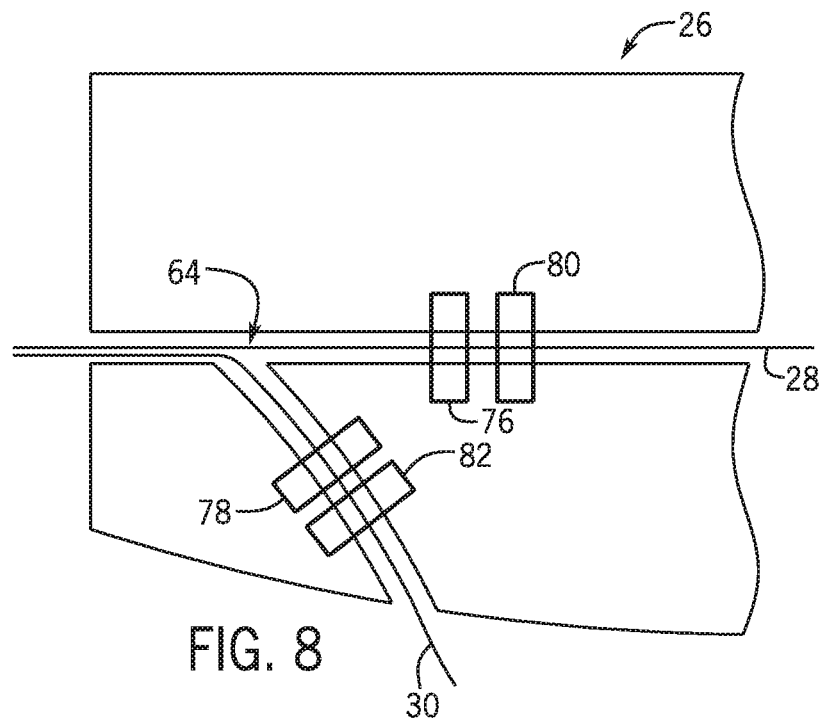
FIG. 8 is a schematic view of a robotic percutaneous system with a wiper positioned proximal the juncture and distal the guide wire drive.

Referring to FIG. 8 in one embodiment wiper assembly 76 is positioned proximal a drive mechanism 80 that drives the guide wire 28 along its longitudinal axis into and out of the vasculature. Stated another way wiper assembly 76 is positioned between juncture 64 and linear drive mechanism 80. In one embodiment wiper assembly 78 is positioned between juncture 64 and linear drive mechanism 82 that drives working catheter 30 along its longitudinal axis.

Figure 9:
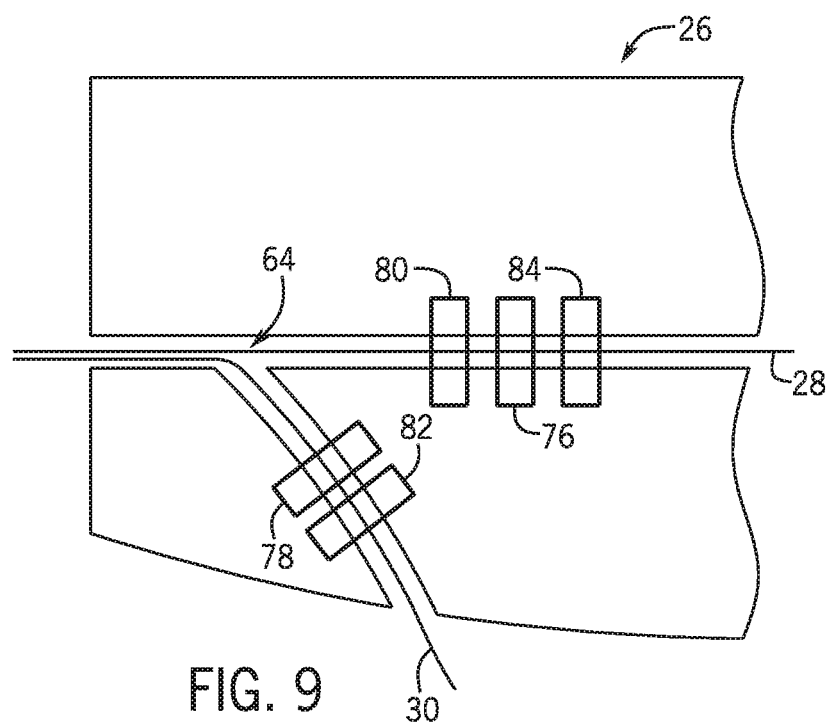
FIG. 9 is a schematic view of a robotic percutaneous system with a wiper positioned proximal the juncture and between the linear guide wire drive and the rotational guide wire drive.

Referring to FIG. 9 in one embodiment wiper assembly 76 is positioned between distal linear drive 80 or stated another linear drive 80 is positioned between juncture 64 and wiper assembly 76. In one embodiment a drive 84 is positioned distal wiper assembly 76. Stated another way wiper assembly is positioned between linear drive 80 and drive 84. In one embodiment drive 84 is a rotational drive mechanism that rotationally drives guide wire 28 about its longitudinal axis. In one embodiment drive 80 and drive 84 are part of a linear drive system that provides linear movement to the guide wire to move guide wire 28 in and out of the vasculature. In one embodiment drive 80 and drive 84 are part of a drive system that provides both linear and rotational drive to guide wire 28. In one embodiment drive 80 and drive 84 are part of a drive system that provides linear drive to guide wire 28.

Figure 10:
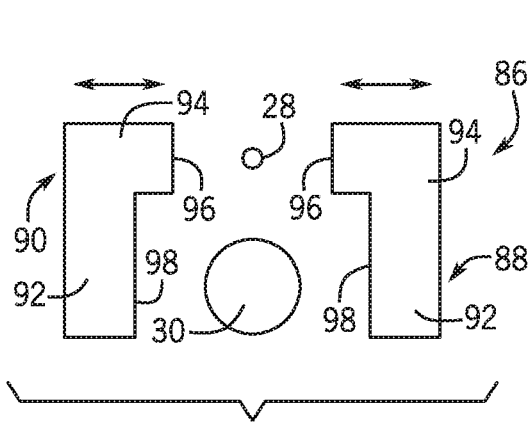
FIG. 10 is a cross sectional view of the wiper material for multiple percutaneous device wiper.

Referring to FIG. 10 wiper material 86 includes a wiper that may be used as wiper material is wiper mechanism 36 or in any other wiper at or distal juncture 64 in which both guide wire 28 and catheter 30 are wiped by a wiper assembly 36. In one embodiment wiper material 86 includes a first wiper 88 and a second wiper 90 that moves toward and away from each other to engage guide wire 28 and catheter 30. First wiper 88 and second wiper 90 each include a first portion 94 and a second portion 92 that engage respectively guide wire 28 and catheter 30. First portions 94 include a wiping surface 96 and second portion 92 include a wiping surface 98. When first wiper 88 and second wiper 90 move toward each other surfaces 96 of first portions 94 are closely adjacent one another in direct contact with guide wire 28. In one embodiment surfaces 96 are sufficiently pliant such that surfaces 86 surround guide wire 28 about its circumference to wipe the entire outer surface of guide wire 28 as guide wire 28 moves relative to wiping mechanism 36 or 76 or 78 along its longitudinal axis.

Figure 10A:
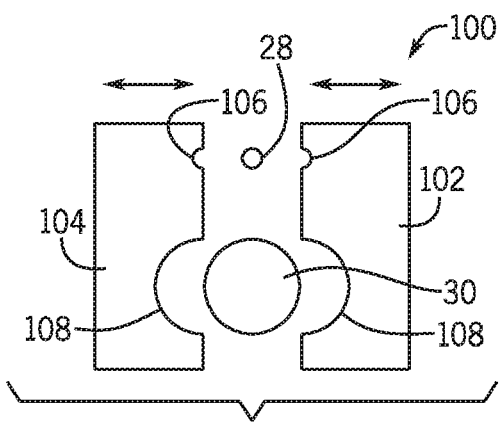
FIG. 10A is a cross sectional view of a wiper material for multiple percutaneous device wiper.

Referring to FIG. 10A a wiper system 36 may include a material 100 that includes a first member 102 and a second member 104 that move toward and away from one another toward the longitudinal axis of guide wire 28 and catheter 30. Each member 102 and 104 include a first recess 106 to receive the outer surface of guide wire 28 and a second recess 108 to receive the outer diameter of catheter 30. In one embodiment recess 106 and recess 108 have a radius that is equal to the radius of guide wire 28 and catheter 30 respectively. In one embodiment recess 106 and recess 108 have a radius that is less than the radius of guide wire 28 and catheter 30 respectively. In one embodiment recess 107 and recess 108 is made of a pliant material that forms fully engages the entire outer circumference of a portion of guide wire 28 and catheter 30 respectively. In this manner the entire outer surface of guide wire 28 and catheter 30 are wiped as the guide wire 28 and catheter 30 move relative to the wiper system 36 along their longitudinal axis.

In one embodiment surfaces 96, 98 or 106,108 are a distance apart so that that they form a first region and a second region respectively having different distances between the two to accommodate different diameter sized guide wire and flexible percutaneous devices.

Figure 11:
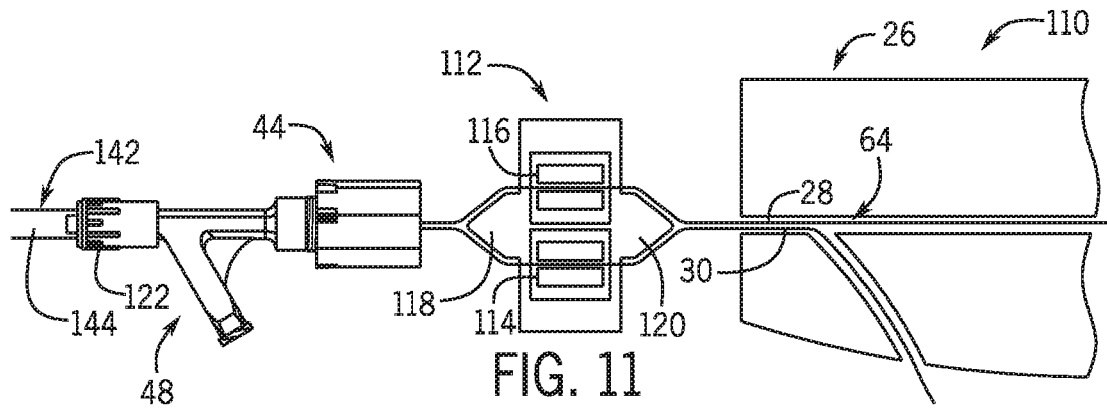
FIG. 11 is a cross sectional top view of a wiper system separating multiple percutaneous devices.

Referring to FIG. 11 a wiper system 110 includes a cassette 26 operatively linearly driving guide wire 28 and catheter 30 along their longitudinal axis through a wiper system 112 having a first wiper 116 and a second wiper 114. Where first wiper 116 wipes guide wire 28 and second wiper 114 wipes catheter 30 as the guide wire and catheter 30 move along their respective liner axis relative to the first wiper 116 and second wiper 114. Each wiper 116 and 114 include wiper elements as described herein. A diverter 118 and 120 operatively guides guide wire 28 and catheter 30 to respective first wiper 116 and second wiper 114 as the guide wire 28 and catheter 30 are moved along their longitudinal axis where first wiper 116 and second wiper 114 are located intermediate juncture 64 and the y-connector 48 and/or hemostasis valve 44. In one embodiment a guide catheter 142 is positioned on the distal end 122 of the y-connector. The guide wire 28 and catheter 30 being moved within a lumen 144 of the guide catheter by a drive mechanism in cassette 26. In one embodiment FIG. 11 is not to scale and the separation of guide wire 28 and catheter 30 is minimal and just sufficient to align the guide wire and catheter within the recesses formed by features 106 and 108 as described herein.

Figure 12:
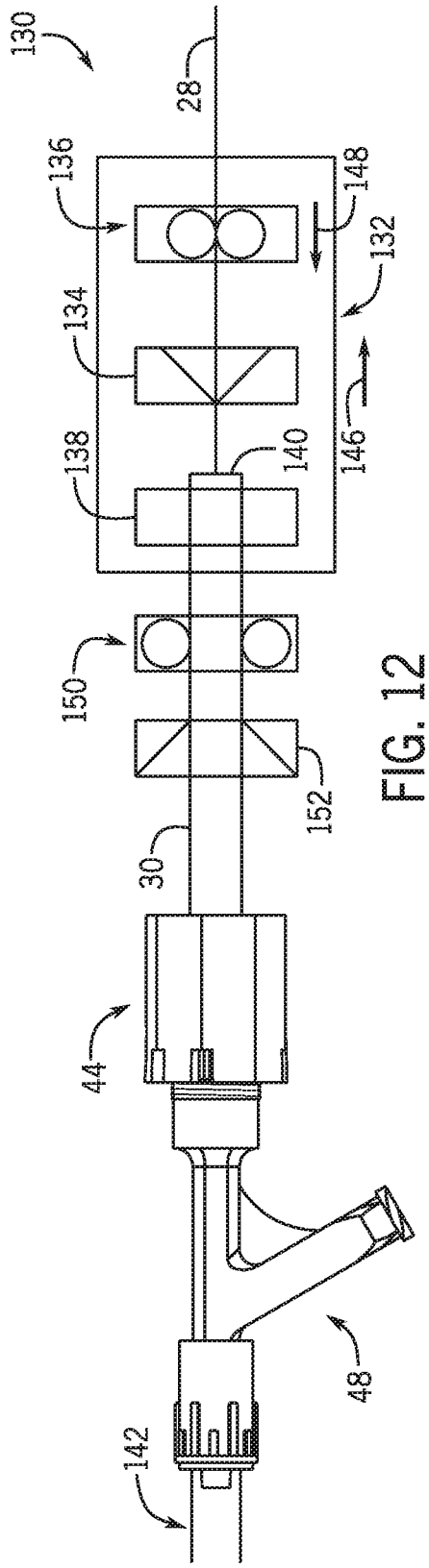
FIG. 12 is a schematic view of a dual wiper system for an over the wire system.

Referring to FIG. 12 a wiper system 130 for a guide wire and catheter includes a housing 132 including a wiper 134 and a drive 136. This wiper system is used on an over the wire device in which catheter 30 extends over guide wire 28. In this over the wire system wiper 134 includes one of the wiper materials as described herein. In one embodiment a holder or seal 138 operatively positions a proximal end 140 of catheter 30 within housing 132. Housing 132 supports guide wire drive 136 and guide wire wiper 134. A catheter drive 150 moves catheter 30 along its longitudinal axis toward and away from y-connector 48. As the proximal end 140 of catheter 30 moves away from y-connector 48 housing 132 moves along with proximal end 140 away from y-connector as well. A catheter wiper 152 operatively is fixed in location relative to y-connector 48 and wipes the outer surface of catheter 30 as proximal end 140 is moved away from y-connector 48. As housing 132 moves away from y-connector 48 linear drive 136 moves guide wire 28 toward y-connector 48 at the same speed as housing 132 moves away from y-connector 48 such that guide wire 28 is stationary with respect to y-connector 48. Since housing 132 is moving away from y-connector 48 and guide wire 28 is remaining stationary with respect to y-connector 48 wiper 134 will wipe the outer surface of guide wire as housing 132 moves away from the y-connector.

While system 130 has been described with respect to a guide wire 28 and a catheter having a lumen receiving the guide wire therein, the system would also work if guide wire 28 were another catheter. In one embodiment another catheter could be in its own housing with a wiper and drive intermediate guide wire housing 132 and catheter 30. Stated another way the system would work with multiple telescoping catheter devices.

Figure 16:
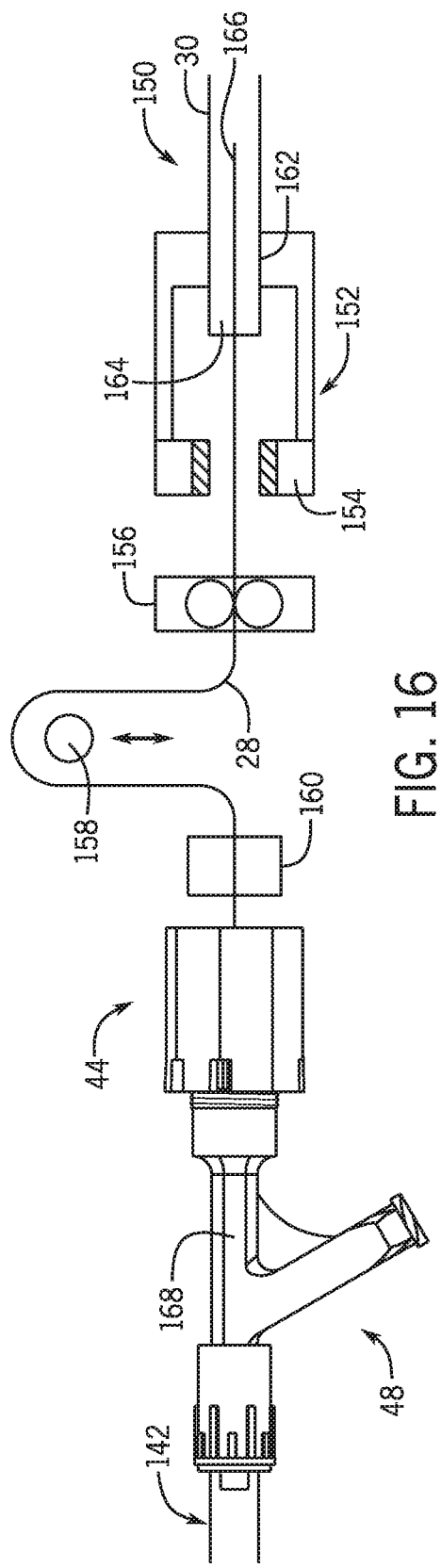
FIG. 16 is a schematic view of a wiper module for a first percutaneous device being removably inserted into a second percutaneous device.

Referring to FIG. 16 a wiper system 150 includes a housing 152 supporting a wiper 154 and a holder 162 for holding a distal end 164 of catheter 30. Wiper system 150 is used in one embodiment for a rapid exchange catheter that rides along the guide wire 28 on a mono-rail type support as is known in the art. A guide wire manager includes a movable guide 158 that includes one or more elements that manage the entire length of the guide wire 28 extending from the y-connector 48 to the proximate end 166 of the guide wire. Guide 158 moves toward and away from a longitudinal axis of guide wire 28 when guide wire 28 is coaxial with a lumen of a leg 168 of y-connector to move any bucking portion or extra length of guide wire out of the way of loader 152. In one embodiment guide 158 moves a portion of guide wire 28 in a direction away from the direction of gravity. In one embodiment guide 158 moves a portion of guide wire 28 in a direction perpendicular to the direction of gravity. In one embodiment guide 158 removably positions a portion of the guide wire in a holder. A brake 160 holds a portion of guide wire in a fixed position relative to y-connector 48 and the portion of guide wire 28 between drive 156 is moved out of the way of an axis extending between drive 156 and y-connector leg 168 such that proximal end 166 is positioned within the rapid exchange portion loader 152. A linear drive 156 drives proximal end 166 of guide wire 28 away from y-connector 48 toward and into engagement with distal end 164 of catheter 30. A wiper 154 wipes the outer periphery of guide wire 28 as described herein. As guide wire 28 is moved away from y-connector 48 guide 158 moves toward a longitudinal axis defined by leg 168 of y-connector until the guide wire is on the same longitudinal axis as leg 168. Guide 158 then moves out of the way to allow catheter 30 to be driven along guide wire 28 through y-connector 48 and into guide catheter 142.

In one embodiment guide wire 28 is fully inserted into catheter 30 such that the longitudinal axis of the guide wire 28 is co-linear with the lumen of leg 168 of Y-connector 48. In this manner guide 158 is moved out of the way of the longitudinal axis of the guide wire 28. Once guide wire 158 is fully inserted within catheter 30 if it is an over the wire catheter or fully extended if a rapid exchange catheter such that the proximal end 166 of the guide wire is furthest from Y-connector wiper 154 engages the outer surface of the guide wire and housing 152 is moved along the longitudinal axis of guide wire 28 in a direction away from y-connector 48 such that the wipers of wiper 154 wipes the outer surface of the guide wire.

Figure 14:
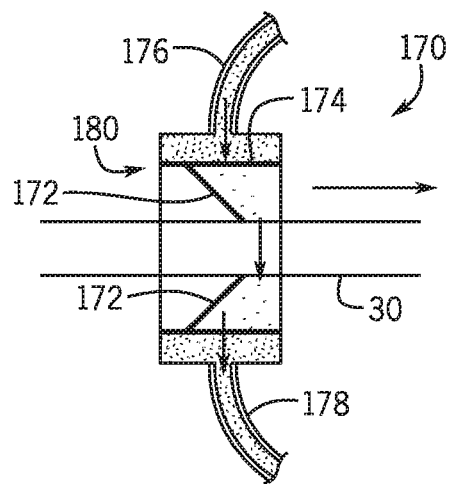
FIG. 14 is a schematic view of a wiper module with a wiper element engaged with a flexible percutaneous device.
Figure 15:
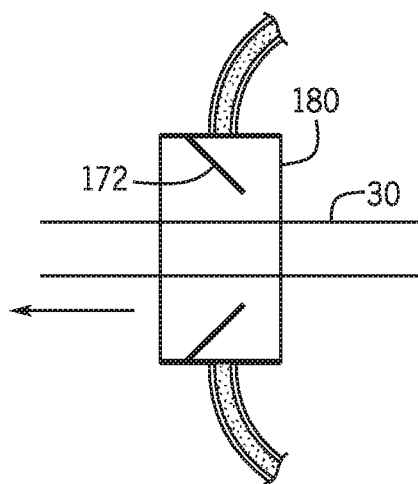
FIG. 15 is the schematic view of a wiper module with a wiper element disengaged with a flexible percutaneous device.

Referring to FIG. 14 and FIG. 15. A wiper system 170 includes wiper elements 172 that operatively engage and wipe catheter 30 but could also be used to operatively engage and wipe guide wire 28. A fluid 174 is introduced through a conduit 176 into wiper housing 180 and flows around the outer periphery of catheter 30 and exits through a drain conduit 178. Catheter 30 is wiped by elements 172 as catheter 30 is moved away from the y-connector and cleaned by fluid 174. Referring to FIG. 15. wiping elements 172 move away from catheter 30 as catheter is driven by a drive mechanism toward and through y-connector 48 into guide catheter 142. In one embodiment wipers 172 are not moved but operate to only wipe catheter 30 as it moves in one direction. In one embodiment wiper elements 172 only wipe when the catheter 30 is moved in a direction away from the y-connector. In one embodiment wiper elements 172 only wipe catheter 30 when the catheter is moved in a direction toward the y-connector. In one embodiment wiper element or elements wipe catheter 30 both when the catheter is moved away from the y-connector and moved toward the y-connector. In one embodiment housing 180 does not include fluid cleaning feature. In one embodiment housing 180 moves back and forth along the longitudinal axis of catheter 30.

In one embodiment the rate of fluid introduced into the cavity of the wiper assembly is robotically controlled based on the length of percutaneous device cleaned and the rate in which the percutaneous device moves through the wiper assembly. In one embodiment, fluid is introduced when the percutaneous device is stationary to clean the wiper surfaces. A flutter valve or umbrella valve may be used to control the flow of the fluid within the wiper assembly. In one embodiment the fluid is introduced at a pressure greater than that of gravity. In one embodiment the fluid is introduced as a high velocity flow or spray. In one embodiment the fluid is introduced in a pulsating means. In one embodiment the fluid forms a bath about the circumference of the percutaneous device within the wiper assembly. In one embodiment the fluid is ultrasonically agitated to aid in the cleaning of the percutaneous device and/or wipers. In one embodiment the fluid may be heated above room temperature.

Figure 13:
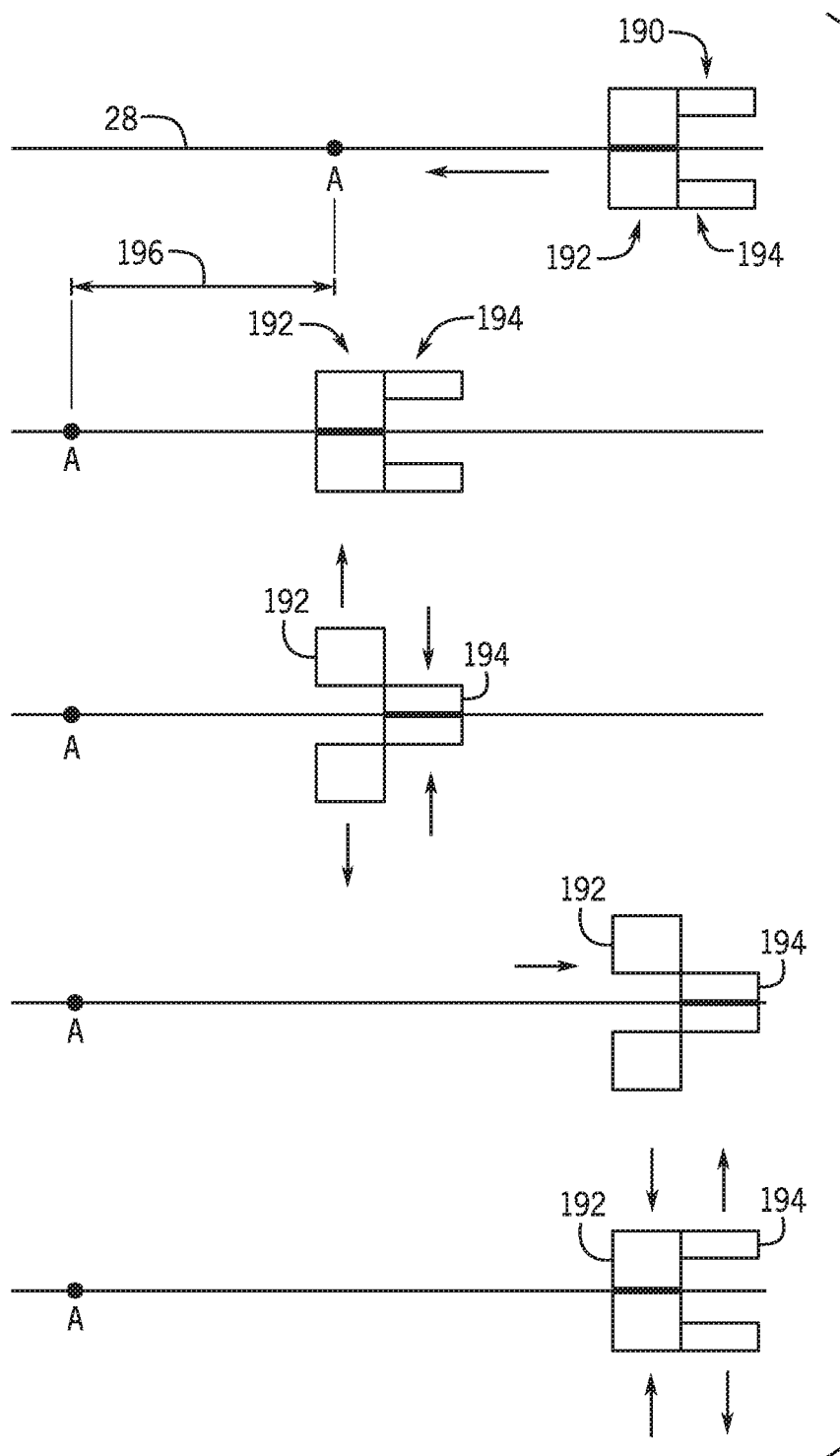
FIG. 13 is a schematic view of a discrete motion wiper system.

Referring to FIG. 13 a wiper system 190 includes a movable a drive 192 that has a releasable gripper 192 that releasable engages guide wire 28 or catheter 30. Referring to FIG. 13 gripper 192 operatively grips guide wire 28 and moves toward y-connector 48 moving guide wire 28 a distance toward y-connector 48. This is illustrated in FIG. 13 as a point A on guide wire 28 being moved a distance 196. Gripper 192 then releases guide wire 28 and gripper portions move away from the longitudinal axis of guide wire 28. Wiper elements 194 that were disengaged from guide wire 28 are now moved into wiping engagement with guide wire 28 in a direction toward the longitudinal axis of guide wire 28. Drive 192 moves in a direction away from y-connector while wiping elements wipe the outer surface of guide wire 28. Once drive 192 moves away from y-connector a distance 196 the wiping element disengage from the outer surface of guide wire 28 and gripper 192 moves toward the longitudinal axis of guide wire 28 gripping the guide wire 28. The process then repeats. In one embodiment wiper elements 194 are directly connected to gripper 192. In one embodiment wiper elements 194 is in its own housing and moves independent of gripper 192 by a separate motor drive system. In one embodiment wiper elements 194 is similar to wiper system 170 where wiper system 170 moves and wipes as indicated herein in a step wise discrete manner. In one embodiment a releasable gripper holder not shown is used to secure the guide wire as the wiper elements are contacting and wiping the outer surface of the guide wire 28 to ensure that the guide wire does not move along with the wiper elements in a direction along the longitudinal axis of the guide wire.

Referring to FIG. 17 various wiper elements are for use in any of the wiper systems described herein. Referring to FIG. 17A a duck bill pair of elements 200 engage guide wire 28 or catheter 30 (percutaneous device) by having a pair of flexible members contacting the outer surface of the percutaneous device. Elements have some spring force associated with them such that the terminal ends of the wiper elements remain engaged with the outer surface of the percutaneous device. In one embodiment a second pair of duck bill elements 200 are arranged in an opposing orientation to provide wiping of the percutaneous device when the percutaneous device is being moved along its longitudinal axis in a second direction opposite the first direction.

Figure 17A:
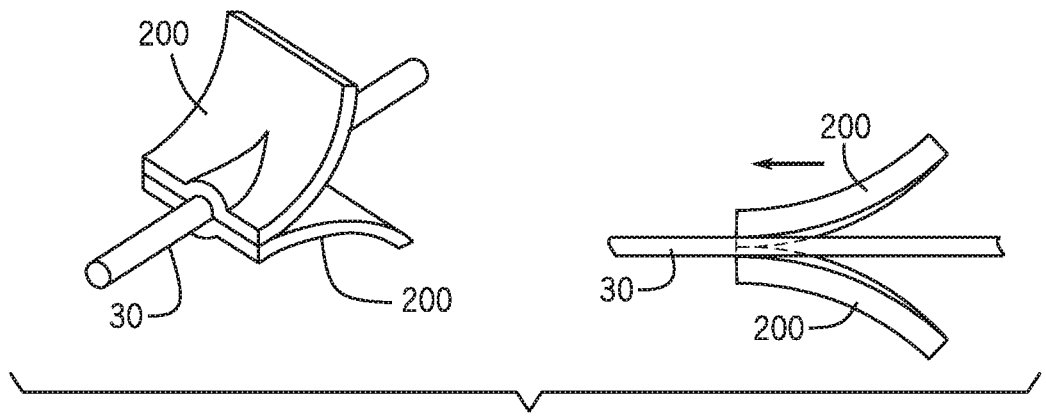
FIG. 17A-17E are a schematic view of wiper materials.
Figure 17B:
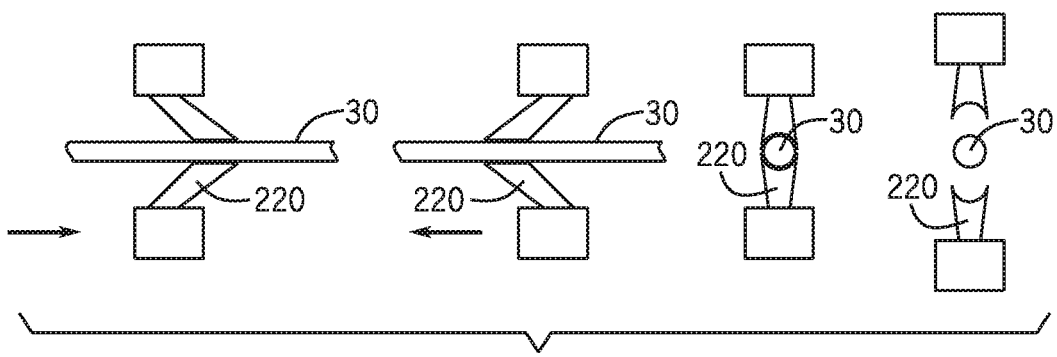
Figure 17C:
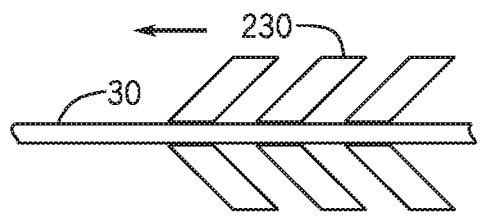

Referring to FIG. 17C a flexible micro lip seal effectively wipes percutaneous device 30 as it moves both toward and away from y-connector along its longitudinal axis. Seal 220 being sufficiently flexible wiper to bend in the direction of movement of the percutaneous device.

Figure 17E:
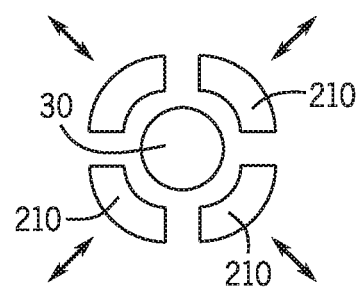
Figure 17D:
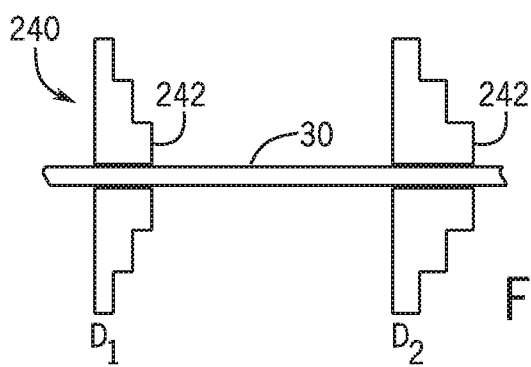

Referring to FIG. 17D a plurality of flexible fingers or blades operatively engage the outer surface of the percutaneous device to provide multiple wiping elements to act on the outer surface of the percutaneous device. Referring to FIG. 17 a flexible bellow member 240 includes a lip portion 242 that extends from a base portion 244 as the percutaneous device moves along its longitudinal axis. Bellow housing member 240 expands in a direction of travel of the percutaneous device. In one embodiment one of the wiper elements as described herein provides an ultrasonic vibration to the percutaneous device sufficient to shed liquid and foreign material from the percutaneous device either alone or in combination with the mechanical wiping of the wiping members. In one embodiment a vacuum is applied to the exit or drain 178 to remove liquid from the wiper assembly 170.

Referring to FIG. 17E split wiper members moves radially toward and away from the longitudinal axis of the percutaneous device 30. The split wiper members may include 2, 3 4 or more members that are moved toward and away from the percutaneous device to effectively wipe the entire circumference of the percutaneous device.

In one embodiment a wiper rotates about the circumference of the percutaneous device and has a wiping surface that removable engages the outer surface of the percutaneous device. In one embodiment the rotary wiper is in a housing that in addition to rotating about the circumference of the percutaneous device also moves relative to the percutaneous device along the longitudinal axis of the percutaneous device. In one embodiment both the percutaneous device and wiper housing that supports moves relative to the Y-connector and the In one embodiment a wiping mechanism is robotically controlled moving the wiper toward and away from the moving percutaneous devices. In one embodiment a wiping member may be robotically controlled in a hemostasis valve such as that shown in FIG. 29 and FIG. 30 of co-pending U.S. application Ser. No. 15/029,115 in which the hemostasis valve is controlled remotely from a user interface. The hemostasis valve may be modified and or another valve may be placed between the hemostasis valve 44 and cassette 26. Stated another way wiper assembly 36 includes a robotic controlled hemostasis valve shown in FIG. 29 and FIG. 30 of U.S. patent application Ser. No. 15/029,115 in which the valve is a wiper assembly that is robotically controlled by rotation of the outer housing. In one embodiment the system includes a controller that automatically engages the wiper with the percutaneous valve upon retraction of a device. In one embodiment the system automatically engages a wiper member upon retraction of a device for more than a predetermined time period and/or predetermined distance.

In one embodiment the user interface includes a wiper control button to provide instructions to the wiper systems to engage and wipe one percutaneous device and/or all the percutaneous devices. In one embodiment a signal is sent to the motors providing the retraction force to increase the force to overcome the friction that results from the wipers engaging the outer surface of the one or more percutaneous devices being wiped. In one embodiment the wiper materials are formed from a hyrdrophobic material and provides a squeegee action to remove foreign matter from the percutaneous device. In one embodiment the wiping material is a hydrophilic material that absorbs liquid from the percutaneous device. In one embodiment a sensor may send a portion of the wiping material for wetness and provide an alert to the user via a user interface to change replace the wipers and/or to automatically wash the wipers in a fluid rinse as described herein.

It is contemplated that the various wiping elements and features of the wiping system be interchangeable with the various systems described herein. In one embodiment Guide wire 28 and catheter 30 are flexible elongated medical devices and are generically referred to herein as percutaneous devices. However other elongated medical devices that are flexible or rigid or in between known in the art are herein referred to as percutaneous devices.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. Any of the features, elements, or components of any of the exemplary embodiments discussed above may be used alone or in combination with any of the features, elements, or components of any of the other embodiments discussed above. It is to be understood that the forms of the invention shown and described herein are to be taken as presently preferred embodiments. Elements and materials may be substituted for those illustrated and described herein, parts and processes may be reversed, and certain features of the invention may be utilized independently, all as would be apparent to one skilled in the art having the benefit of this description of the invention. Changes may be made in the elements described herein without departing form the spirit and scope of the invention as described in the following claims.

What is claimed is:

1. A robotic catheter system, the system comprising:
    a first drive mechanism configured to interact with an elongated medical device to cause the elongated medical device to move along its longitudinal axis;
    a wiper assembly having a first wiping surface configured to move radially toward and away from the longitudinal axis of the elongated medical device, where the first wiping surface is aligned with the longitudinal axis as the first wiping surface moves radially toward and away from the longitudinal axis; and
    a controller to provide a signal to a motor to move the first wiping surface radially toward the longitudinal axis to contact a surface of the elongated medical device to remove fluid from the elongated medical device while the elongated medical device is moved by the first drive mechanism along the longitudinal axis toward the first drive mechanism.

2. The robotic catheter system of claim 1, wherein the first wiping surface is disposed on a roller, and
    wherein the roller is configured to rotate about an axis perpendicular to the longitudinal axis.

3. The robotic catheter system of claim 2, further comprising a roller motor to drive the roller while the elongated medical device is moved by the first drive mechanism along the longitudinal axis toward the first drive mechanism.

4. The robotic catheter system of claim 1, further comprising:
a Y-connector connected to a hemostasis valve, the first wiping surface being positioned intermediate the hemostasis valve and the first drive mechanism.

5. The robotic catheter system of claim 1,
the controller to provide a second signal to the motor to move the first wiping surface away from the longitudinal axis while the elongated medical device is moved by the first drive mechanism along its longitudinal axis toward the first drive mechanism.

6. The robotic catheter system of claim 1, further comprising:
a dispenser to deposit a fluid on the elongated medical device while the elongated medical device is moved by the first drive mechanism along the longitudinal axis.

7. The robotic catheter system of claim 6, wherein the controller is to determine a flow rate of the fluid based on a speed at which the elongated medical device is moved by the first drive mechanism along the longitudinal axis.

8. A robotic catheter system, the system comprising:
a first drive mechanism to move a first percutaneous device;
a first wiper assembly having a first wiping surface;
a controller providing a signal to a motor to move the first wiping surface radially from a position disengaged with the outer surface of the percutaneous device to a position engaged with the outer surface of the percutaneous device as the first percutaneous device moves relative to the first wiper assembly, where a longitudinal axis of the first percutaneous device is aligned with the first wiping surface at the position disengaged with the outer surface of the percutaneous device and at the position engaged with the outer surface of the percutaneous device; and
a cassette comprising a first channel in which the first percutaneous device is disposed and a second channel, where the first channel and the second channel intersect at a juncture.

9. A robotic catheter system according to claim 8, further comprising:
a second drive mechanism to move a second percutaneous device disposed in the second channel; and
a second wiper assembly having a second wiping surface to engage an outer surface of the second percutaneous device as the second percutaneous device moves relative to the second wiper assembly.

10. A robotic catheter system according to claim 9, further comprising:
a wiper system comprising the first wiper assembly and the second wiper assembly; and
a hemostasis valve,
wherein the wiper system is intermediate the juncture and the hemostasis valve.

11. A robotic catheter system according to claim 9, further comprising:
a wiper system comprising the first wiper assembly and the second wiper assembly; and
a Y-connector,
wherein the wiper system is intermediate the juncture and the Y-connector.

12. A robotic catheter system according to claim 9,
wherein the first wiper assembly is intermediate the first drive mechanism and the juncture, and
wherein the second wiper assembly is intermediate the second drive mechanism and the juncture.

13. A robotic catheter system according to claim 12, further comprising:
a third drive mechanism to drive the first percutaneous device, the third drive mechanism being intermediate the first wiper assembly and the juncture.

14. A robotic catheter system according to claim 13, wherein one of the first drive mechanism and the third drive mechanism comprise a linear drive and the other of the first drive mechanism and the third drive mechanism comprise a rotational drive.

15. A method comprising:
controlling a first drive mechanism to move a first percutaneous device along a first channel of a cassette, where the cassette includes a second channel and where the first channel and the second channel intersect at a juncture; and
providing a signal to a motor to move a first wiping surface of a first wiper assembly radially from a position disengaged with an outer surface of the first percutaneous device to a position engaged with the outer surface of the first percutaneous device as the first percutaneous device moves along the first channel and relative to the first wiper assembly, where longitudinal axis of the first percutaneous device is aligned with the first wiping surface at the position disengaged with the outer surface of the percutaneous device and at the position engaged with the outer surface of the percutaneous device.

16. A method according to claim 15, further comprising:
controlling a second drive mechanism to move a second percutaneous device along the second channel; and
providing a second signal to a second motor to engage a second wiping surface of a second wiper assembly with an outer surface of the second percutaneous device as the second percutaneous device moves along the second channel and relative to the second wiper assembly.

17. A method according to claim 16, wherein a wiper system comprising the first wiper assembly and the second wiper assembly is intermediate the juncture and a hemostasis valve while the first percutaneous device moves along the first channel and the second percutaneous device moves along the second channel.

18. A method according to claim 16, wherein a wiper system comprising the first wiper assembly and the second wiper assembly is intermediate the juncture and a Y-connector while the first percutaneous device moves along the first channel and the second percutaneous device moves along the second channel.

19. A method according to claim 16, further comprising:
controlling a third drive mechanism to rotate the first percutaneous device within the first channel.

20. A method according to claim 19, wherein one of the first drive mechanism and the third drive mechanism is intermediate the first wiper assembly and the juncture.

* * * * *